(12) United States Patent
Doverskog et al.

(10) Patent No.: US 9,801,894 B2
(45) Date of Patent: Oct. 31, 2017

(54) STEROID COMPOUND FOR USE IN THE TREATMENT OF HEPATIC ENCEPHALOPATHY

(71) Applicant: Umecrine Cognition AB, Solna (SE)

(72) Inventors: Magnus Doverskog, Stockholm (SE); Hanns Möhler, Maennedorf (CH); Vicente Felipo, Naquera (ES); Torbjörn Bäckström, Umeå (SE)

(73) Assignee: Umecrine Cognition AB, Solna (SE)

(*) Notice: Subject to any disclaimer, the term of this patent is extended or adjusted under 35 U.S.C. 154(b) by 0 days.

(21) Appl. No.: 15/352,035

(22) Filed: Nov. 15, 2016

(65) Prior Publication Data
US 2017/0056416 A1    Mar. 2, 2017

Related U.S. Application Data

(63) Continuation of application No. 15/114,972, filed as application No. PCT/GB2015/050060 on Jan. 14, 2015.

(30) Foreign Application Priority Data

Jan. 29, 2014 (SE) ........................ 1450089

(51) Int. Cl.
A61K 31/568 (2006.01)
A61K 31/4375 (2006.01)
A61K 45/06 (2006.01)
A61K 31/198 (2006.01)
A61K 31/216 (2006.01)
A61K 31/437 (2006.01)
A61K 31/7016 (2006.01)

(52) U.S. Cl.
CPC .......... *A61K 31/568* (2013.01); *A61K 31/198* (2013.01); *A61K 31/216* (2013.01); *A61K 31/437* (2013.01); *A61K 31/4375* (2013.01); *A61K 31/7016* (2013.01); *A61K 45/06* (2013.01)

(58) Field of Classification Search
None
See application file for complete search history.

(56) References Cited

U.S. PATENT DOCUMENTS 2,713,061 A   7/1955   Kathol
3,173,932 A   3/1965   Cantrall et al.
6,596,885 B2  7/2003   Claussner et al.

(Continued)

FOREIGN PATENT DOCUMENTS

FR   1 463 755 A      7/1966
WO   94/27608 A1     12/1994

(Continued)

OTHER PUBLICATIONS

Bassett, Gastroenterology, Nov. 1987; 93(5): 1069-77, abstract only.*

(Continued)

*Primary Examiner* — Layla D Berry
(74) *Attorney, Agent, or Firm* — McCarter & English, LLP; Steven G. Davis; Xin Zhang

(57) ABSTRACT

The present invention provides the steroidal compound 3☐-ethynyl-3☐-hydroxyandrostan-17-one oxime, or a pharmaceutically acceptable salt thereof, for use in treatment of hepatic encephalopathy.

27 Claims, 9 Drawing Sheets

(56) References Cited

U.S. PATENT DOCUMENTS

| | | | |
|---|---|---|---|
| 6,852,710 | B2 | 2/2005 | Rao et al. |
| 8,580,983 | B2 | 11/2013 | Backstrom et al. |
| 9,200,028 | B2 | 12/2015 | Backstrom et al. |
| 2008/0119416 | A1* | 5/2008 | Backstrom ............. C07J 1/00 514/26 |

FOREIGN PATENT DOCUMENTS

| | | |
|---|---|---|
| WO | 99/45931 A1 | 9/1999 |
| WO | 03059357 A1 | 7/2003 |
| WO | 2006/056794 A1 | 6/2006 |
| WO | 2007103162 A2 | 9/2007 |
| WO | 2008063128 A1 | 5/2008 |
| WO | 2009142594 A1 | 11/2009 |
| WO | 2010040020 A1 | 4/2010 |
| WO | 2010144498 A2 | 12/2010 |
| WO | 2015/048818 A1 | 4/2015 |

OTHER PUBLICATIONS

Prakash, Nature Reviews, Gastroenterology & Hepatology, vol. 7, Sep. 2010, pp. 515-525.*

Alba Gonzalez-Usano, et al., Pregnenolone Sulfate Restores the Glutamate-Nitric-Oxide-cGMP pathway and Extracellular GABA in Cerebellum and Learning and Motor Coordination in Hyperammonemic Rats, ACS Chemical Neuroscience, 5(2):100-105, Nov. 20, 2013.

Samir Ahboucha, et al., Role of Endogenous Benzodiazepine Ligands and Their GABA-A-Associated Receptors in Hepatic Encephalopathy, Metabolic Brain Disease, 20(4):425-437, Dec. 1, 2005.

Ahboucha, S., et al., Unequivocal Evidence for a Role of Neurosteroids with Positive Allosteric Modulatory Properties at the GABA-A Receptor in the Pathogenesis of Hepatic Encephalopathy, Hepatology, vol. 38, No. 48, p. 178, Jan. 1, 2003.

Johansson, Maja et al; GR3027 antagonizes GABAA receptor-potentiating neurosteroids and restores spatial learning and motor coordination in rats with chronic hyperammonemia and hepatic encephalopathy, Am J Physiol Gastrointest Liver Physiol 309: G400-G409, 2015.

Johansson, Maja et al., GABAA receptor modulating steriod antagonists (GAMSA) are functional in vivo, Journal of Steroid Biochemistry & Molecular Biology, 169:98-105, 2015.

Wang, M.D., et al, The inhibitory effects of allopregnanolone and pregnanolone on the population spike, evoked in the rat hippocampal CA1 stratum pyramidale in vitro, can be blocked selectively by epiallopregnanolone, Acta Physiol Scand, 169:333-341, 2000.

Wang, et al, 3Beta-Hydroxypregnane Steriods Are Pregnenolone Sulfate-Like GABAA Receptor Antagonists, The Journal of Neuroscience, 22(9):3366-3375, 2002.

Press Release: Phase 1 data with GR3027 in hepatic encephalopathy demonstrating safety, tolerability and CNS target engagement: Nov. 3, 2016.

Press Release: Preclinical results of the candidate drug GR3027 aimed for the treatment of hepatic encephalopathy: Aug. 19, 2015.

Ahboucha, et al., Neuroactive steroids and fatigue severity in patients with primary biliary cirrhosis and hepatitis C, Neurogastroenterol. Motil., 20:671-679, 2008.

Ahboucha, et al., Indomethacin improves locomotor deficit and reduces brain concentrations of neuroinhibitory steriods in rats following portacaval anastomosis, Neurogastroenterol. Motil., 20:949-957, 2008.

Ahboucha, et al., Increased levels of pregnenolone and its neuroactive metabolite allopregnanolone in autopsied brain tissue from cirrhotic patients who died in hepatic coma, Neurochemistry International, 49:372-378, 2006.

Ahboucha et al., The neurosteriod system: Implication in the pathophysiology of hepatic encephalopathy, Neurochemistry International, 52:575-587, 2008.

Ahboucha et al., Reduced brain levels of DHEAS in hepatic coma patients: Significance for increased GABAergic tone in hepatic encephalopathy, Neurochemistry International, 61:48-53, 2012.

Ahboucha et al., GABAergic neurosteriods: The "endogenous benzodiazepines" of acute liver failure, Neurochemistry International, 60:707-714, 2012.

Cordoba et al., Characteristics, risk factors, and mortality of cirrhotic patients hospitalized for hepatic encephalopathy with and without acute-on-chronic liver failure (ACLF), Journal of Hepatology, 60:275-281, 2014.

* cited by examiner

STEROID COMPOUND FOR USE IN THE TREATMENT OF HEPATIC ENCEPHALOPATHY

RELATED APPLICATIONS

This application is a Continuation of U.S. application Ser. No. 15/114,972, filed on Jul. 28, 2016. U.S. application Ser. No. 15/114,972 is the 35 U.S.C. §371 national stage filing of International Application No. PCT/GB2015/050060, filed Jan. 14, 2015, which claims priority to Swedish Application No. 1450089-6, filed Jan. 29, 2014. The entire contents of the foregoing applications are hereby incorporated by reference.

FIELD OF THE INVENTION

The present invention concerns a steroid compound for use in treatment of hepatic encephalopathy.

BACKGROUND OF THE INVENTION

Hepatic encephalopathy (HE) is a serious neuropsychiatric and neurocognitive complication in acute and chronic liver disease. HE is a significant and increasing health care problem due to the large and increasing prevalence of chronic liver disease. HE is characterized by impairments of the sleep-wake cycle, cognition, memory, learning, motor coordination, consciousness, decreased energy levels and personality change, ranging from minimal HE (MHE) to overt HE (OHE). MHE is manifested with cognitive impairment and has detrimental effects on health related quality of life and the ability to perform complex tasks such as driving. In addition, OHE is clinically manifested with mental and motor disorders and the symptoms ranges from disorientation through sedation and coma.

Naturally occurring steroids are subject to intense metabolism and are typically not suitable for oral administration. The metabolites of the endogenous steroid hormones pregnenolone, progesterone, deoxycorticosterone, cortisone and cortisol, known as pregnenolones as well as the metabolites of testosterone, androstenedione and dehydroepiandrosterone, have all been the subject of various studies, at least partially elucidating their role in the neurological signal system in mammals. The steroid metabolites induce CNS symptoms and disorders and steroids act as positive modulators on the gamma-aminobutyric acid receptor-chloride ionophore (GABA$_A$-R) complex and are therefore called GABA$_A$ receptor modulating steroids (GAMS).

Certain steroids have been shown to be specific GABA$_A$ receptor enhancers. Examples of these steroids can inter alia be found in WO 2008/063128. Some of these steroids are potent and have e.g. been shown to have an ability to induce amnesia, sedation and anesthesia in pharmacological dose. WO 99/45931 and WO 03/059357 disclose antagonistic effects of steroids. Wang et al. 2000 (Acta Physiol Scand 169, 333-341) and Wang et al. 2002 (J Neurosci 22(9):3366-75) disclose antagonistic effects of 3β-OH-5α-pregnan-20-one and other 3β-OH-5α/β pregnan steroids. WO2006/056794 and WO2010/144498 discloses use of compounds for treatment of liver decompensation, hepatic encephalopathy and portal hypertension. There is a need to provide new and effective therapeutic treatments for hepatic encephalopathy and related disorders

DESCRIPTION OF THE INVENTION

The present invention provides the compound 3α-ethynyl-3β-hydroxyandrostan-17-one oxime

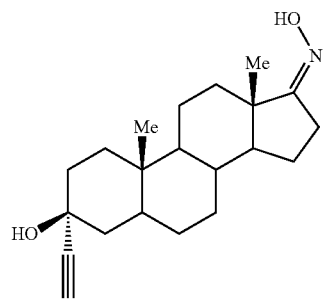 [SMILES: C#C[C@]1(O)CC[C@@]2(C)C(CCC3C2CC[C@]2(C)/C(=N\O)CCC32)C1]

or a pharmaceutically acceptable salt thereof, for use in treatment of hepatic encephalopathy.

3α-Ethynyl-3β-hydroxyandrostan-17-one oxime belongs to a class of compounds known as GABA$_A$ receptor modulating steroid antagonists (GAMSAs).

We have found that 3α-ethynyl-3β-hydroxyandrostan-17-one oxime is able to selectively inhibit the positive modulation of the GABA$_A$ receptor by endogenous steroids such as allopregnanolone and tetrahydrodeoxycorticosterone (THDOC). These steroids are known to induce sedation, cognitive impairment and motor disturbances, and their concentration in the brain is increased in patients with liver disease-induced hyperammonemia and HE.

However, we have also found that 3α-ethynyl-3β-hydroxyandrostan-17-one oxime does not have an antagonistic effect towards the action of gamma-aminobutyric acid (GABA) at the GABA$_A$ receptors. This surprising selectivity is advantageous from a safety perspective as inhibition of GABA binding at the GABA$_A$ receptors can lead to side-effects, including convulsions.

Furthermore, 3α-ethynyl-3β-hydroxyandrostan-17-one oxime acts on both the α1 and α5 GABA$_A$ receptor subtypes and so is able to exert a positive effect on both the motor and cognitive impairment, and the sedative effects, that result from the over-activation of GABA$_A$ receptors. The positive effect of 3α-ethynyl-3β-hydroxyandrostan-17-one oxime on motor and cognitive impairment has been illustrated in two animal models of HE (hyperammonemia and porta-caval anastomosis in rats vide infra).

Unlike existing treatments for HE, 3α-ethynyl-3β-hydroxyandrostan-17-one oxime does not affect ammonia levels in vivo. Therefore, there is clearly also potential for it's complementary use in therapy.

Accordingly, there is good basis to believe that 3α-ethynyl-3β-hydroxyandrostan-17-one oxime is particularly well-suited to the treatment of HE and related disorders.

Figure 3:
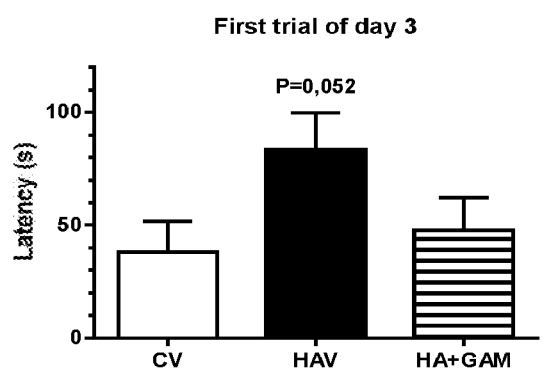

FIG. 3 shows that 3α-ethynyl-3β-hydroxyandrostan-17-one oxime, in the Morris water maze test, restores special memory of hyperammonemic rats. The figure shows the time to find the platform on the first trial of day 3. Values are the mean±SEM of 8 rats per group. HAV versus CV p=0.052. CV=control rats treated with vehicle; HAV= hyperammonemic rats treated with vehicle; HA+GAM= hyperammonemic rats treated with 3α-ethynyl-3β-hydroxyandrostan-17-one oxime.

Figure 4:
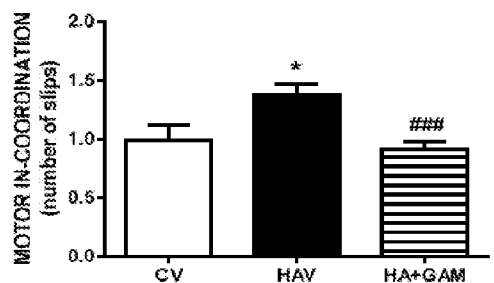

FIG. 4 shows that 3α-ethynyl-3β-hydroxyandrostan-17-one oxime restores motor coordination of hyperammonemic rats. Values are the mean±SEM of 15 rats per group. Values significantly different from CV are indicated by *, $p<0.05$, values significantly different from HAV are indicated by ###, $p<0.001$. CV=control rats treated with vehicle; HAV=hyperammonemic rats treated with vehicle; HA+GAM=hyperammonemic rats treated with 3α-ethynyl-3β-hydroxyandrostan-17-one oxime.

Figure 5:
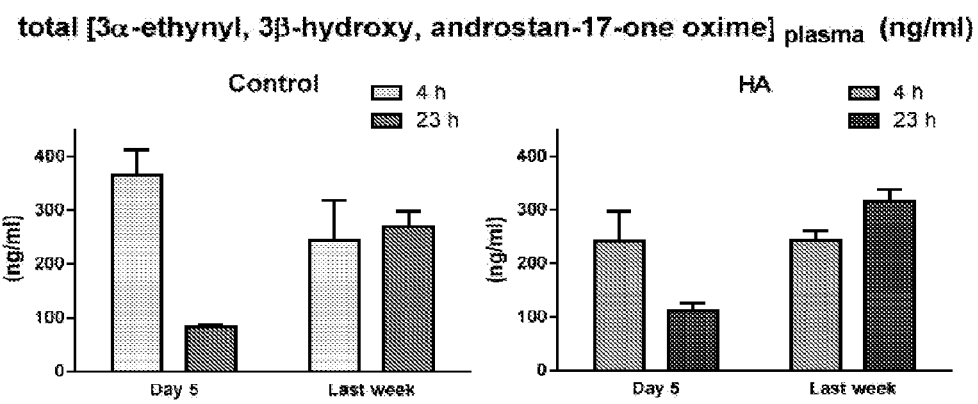

FIG. 5 shows total plasma 3α-ethynyl-3β-hydroxyandrostan-17-one oxime concentrations. Total plasma 3α-ethynyl-3β-hydroxyandrostan-17-one oxime concentrations in control and hyperammonemic rats 4 and 23 hours after the subcutaneous injection of 3α-ethynyl-3β-hydroxyandrostan-17-one oxime on day five and during the last week of treatment with daily injections. HA=Hyper ammonia animals.

Figure 6:
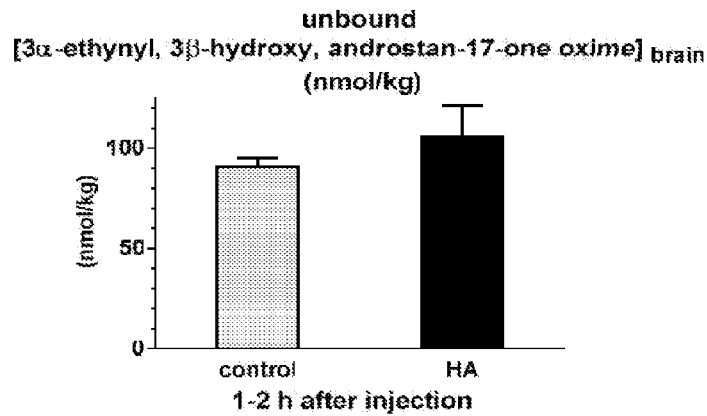

FIG. 6 provides unbound* brain 3α-ethynyl-3β-hydroxyandrostan-17-one oxime concentrations in control and hyperammonemic rats 1-2 hours after the s.c. injection of 3α-ethynyl-3β-hydroxyandrostan-17-one oxime after seven weeks with daily injections of 20 mg/kg.
*Unbound brain concentration=fraction of 3α-ethynyl-3β-hydroxyandrostan-17-one oxime in the brain that is not bound to carrier protein or brain tissue.

Figure 7:
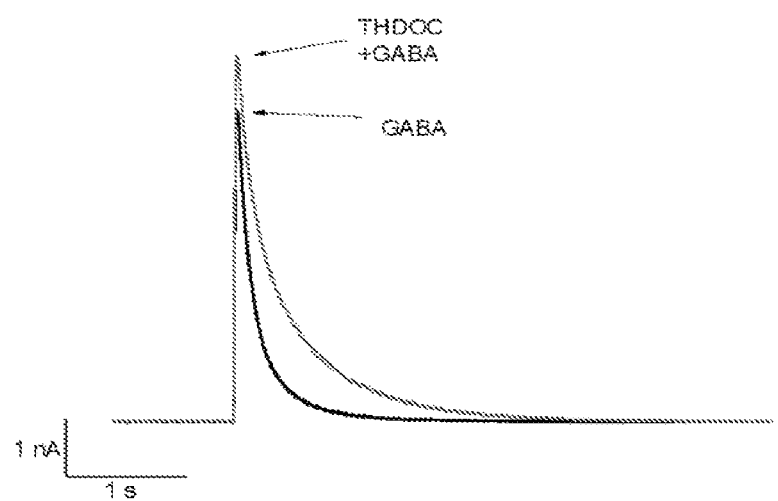

FIG. 7 provides representative electrophysiological measurements showing tetrahydrodeoxycorticosterone (THDOC) enhanced activation of α1β2γ2L GABA$_A$ receptors. HEK-293 cells expressing human α1β2γ2L GABA$_A$ receptors were exposed to 30 μM GABA or 30 μM GABA plus 100 nM THDOC for 40 ms. With THDOC there was a 20 s pre-incubation before application of THDOC+GABA.

Figure 8:
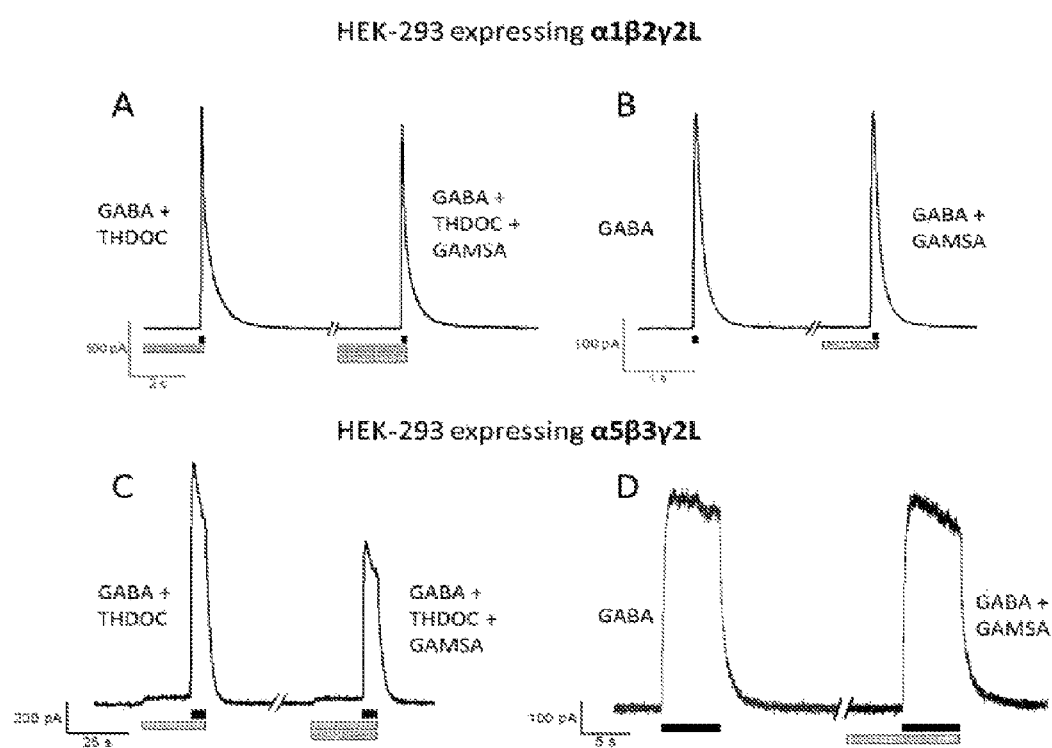

FIG. 8 provides representative electrophysiological measurements showing 3α-ethynyl-3β-hydroxyandrostan-17-one oxime (GAMSA) antagonism of the THDOC enhanced activation of α1β2γ2L and α5β3γ2L GABA$_A$ receptors and no inhibition of GABA. A) 1 μM 3α-ethynyl-3β-hydroxyandrostan-17-one oxime antagonism of the 100 nM THDOC enhanced activation of 30 μM GABA with the α1β2γ2L GABA$_A$ receptor, B) 1 μM 3α-ethynyl-3β-hydroxyandrostan-17-one oxime does not antagonize the 30 μM GABA activation of the α1β2γ2L GABA$_A$ receptor C) 1 μM 3α-ethynyl-3β-hydroxyandrostan-17-one oxime antagonism of the 200 nM THDOC enhanced activation of 0.3 μM GABA with the α5β3γ2L GABA$_A$ receptor; indicating antagonism of THDOC's effect D) 1 μM 3α-ethynyl-3β-hydroxyandrostan-17-one oxime does not antagonize the 0.3 μM GABA activation of the α5β3γ2L GABA$_A$ receptor.

Figure 9:
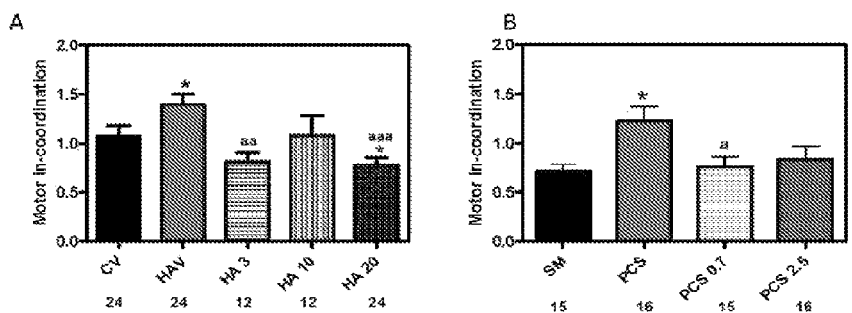

FIG. 9 illustrates the ability of 3α-ethynyl-3β-hydroxyandrostan-17-one oxime to restore motor coordination in hyperammonemic and PCS rats. Motor coordination was assessed using the beam walking test. (A) shows the data for control (CV) or hyperammonemic (HAV) rats treated with vehicle and for hyperammonemic rats treated with 3 (HA3), 10 (HA10) or 20 (HA20) mg/kg of βα-ethynyl-3β-hydroxyandrostan-17-one oxime. (B) shows the data for sham-operated controls (SM) or PCS rats treated with vehicle and for PCS rats treated with 0.7 (PCS0.7) or 2.5 (PCS2.5) mg/kg of 3α-ethynyl-3β-hydroxyandrostan-17-one oxime. Values are the mean±SEM of the number of rats indicated under each bar. Values significantly different from control or sham rats are indicated by asterisks. Values significantly different from hyperammonemic or PCS rats treated with vehicle are indicated by "a". * $p<0.05$; a $p<0.05$; aa $p<0.01$; aaa $p<0.001$.

Figure 10:
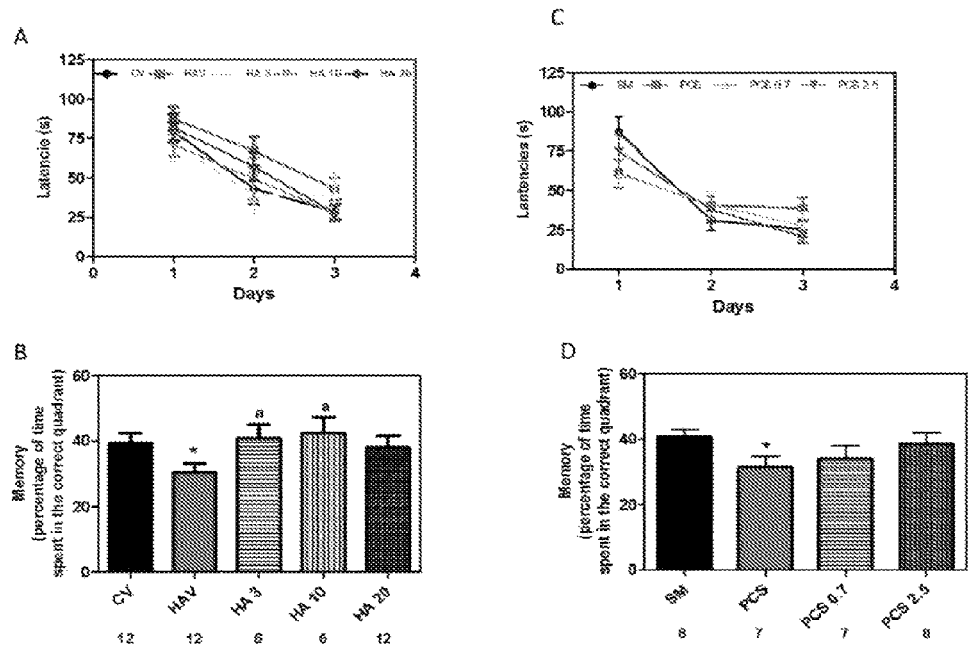

FIG. 10 illustrates the ability of 3α-ethynyl-3β-hydroxyandrostan-17-one oxime to restore spatial memory in the Morris water maze in hyperammonemic and PCS rats. Spatial learning memory in the Morris water maze was assessed in control (CV) or hyperammonemic (HAV) rats treated with vehicle and for hyperammonemic rats treated with 3 (HA3), 10 (HA10) or 20 (HA20) mg/kg of 3α-ethynyl-3β-hydroxyandrostan-17-one oxime (A, B) and in sham-operated controls (SM) or PCS rats treated with vehicle and for PCS rats treated with 0.7 (PCS0.7) or 2.5 (PCS2.5) mg/kg of 3α-ethynyl-3β-hydroxyandrostan-17-one oxime (C,D). (A,C) Escape latencies (in seconds) to reach the platform during the different sessions. (B,D) Time spent (%) in the correct quadrant during the memory test. Values are the mean±SEM of the number of rats indicated under each bar. Values significantly different from control or sham rats are indicated by asterisks. Values significantly different from hyperammonemic or PCS rats treated with vehicle are indicated by "a". * $p<0.05$; a $p<0.05$.

Figure 11:
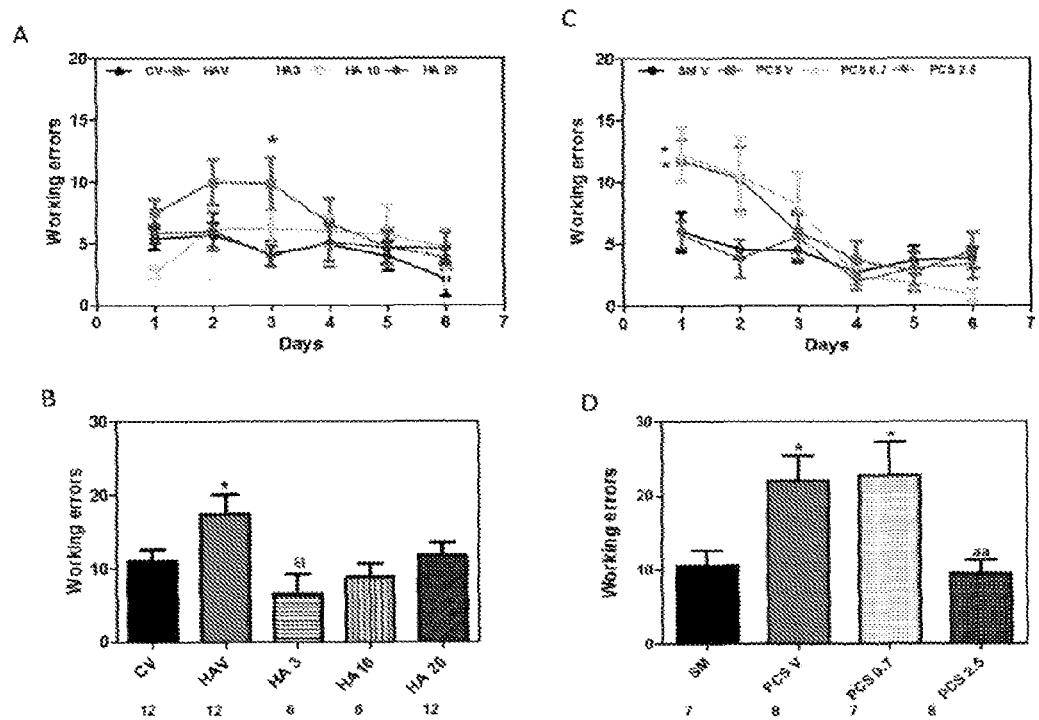

FIG. 11 illustrates the ability of 3α-ethynyl-3β-hydroxyandrostan-17-one oxime to restore spatial learning in the radial maze in hyperammonemic and PCS rats. Spatial learning in the radial maze was assessed in control (CV) or hyperammonemic (HAV) rats treated with vehicle and for hyperammonemic rats treated with 3 (HA3), 10 (HA10) or 20 (HA20) mg/kg of 3α-ethynyl-3β-hydroxyandrostan-17-one oxime (A, B) and in sham-operated controls (SM) or PCS rats treated with vehicle and for PCS rats treated with 0.7 (PCS0.7) or 2.5 (PCS2.5) mg/kg of 3α-ethynyl-3β-hydroxyandrostan-17-one oxime (C,D). (A,C) Working errors during the different sessions. (B,D) Working errors during days 1-2. Values are the mean±SEM of the number of rats indicated under each bar. Values significantly different from control or sham rats are indicated by asterisks. Values significantly different from hyperammonemic or PCS rats treated with vehicle are indicated by "a". * $p<0.05$; a $p<0.05$; aa $p<0.01$.

Figure 12:
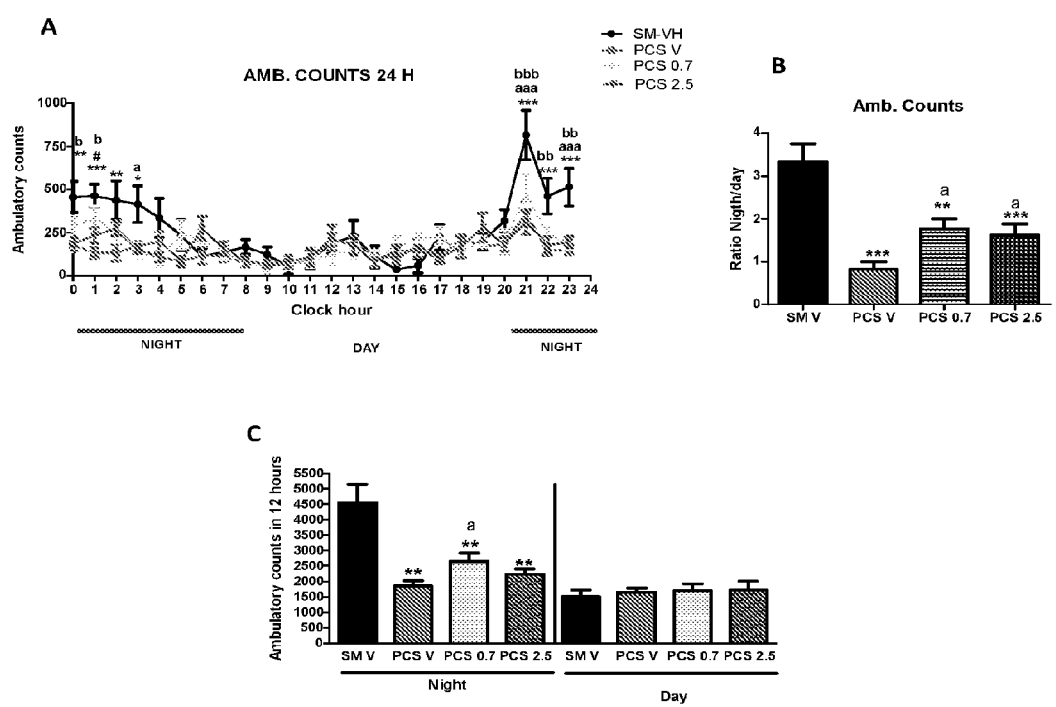

FIG. 12 illustrates the ability of 3α-ethynyl-3β-hydroxyandrostan-17-one oxime to increase spontaneous motor activity during the night and partially restore the circadian rhythm of PCS rats. Motor activity was assessed in sham-operated controls (SM) or PCS rats treated with vehicle or with 0.7 (PCS0.7) or 2.5 (PCS2.5) mg/kg of 3α-ethynyl-3β-hydroxyandrostan-17-one oxime. Motor activity during each hour is shown in A; the ratio of activity during the night and during the day in B and the total activity during the day or the night in C. Lights are turned off at 7:00 pm. Values are the mean±SEM of 8 rats per group. Values significantly different from SM rats are indicated by asterisks; * $p<0.05$;  $p<0.01$; * $p<0.001$. Values significantly different from PCS rats are indicated by a; a $p<0.05$.

Figure 13:
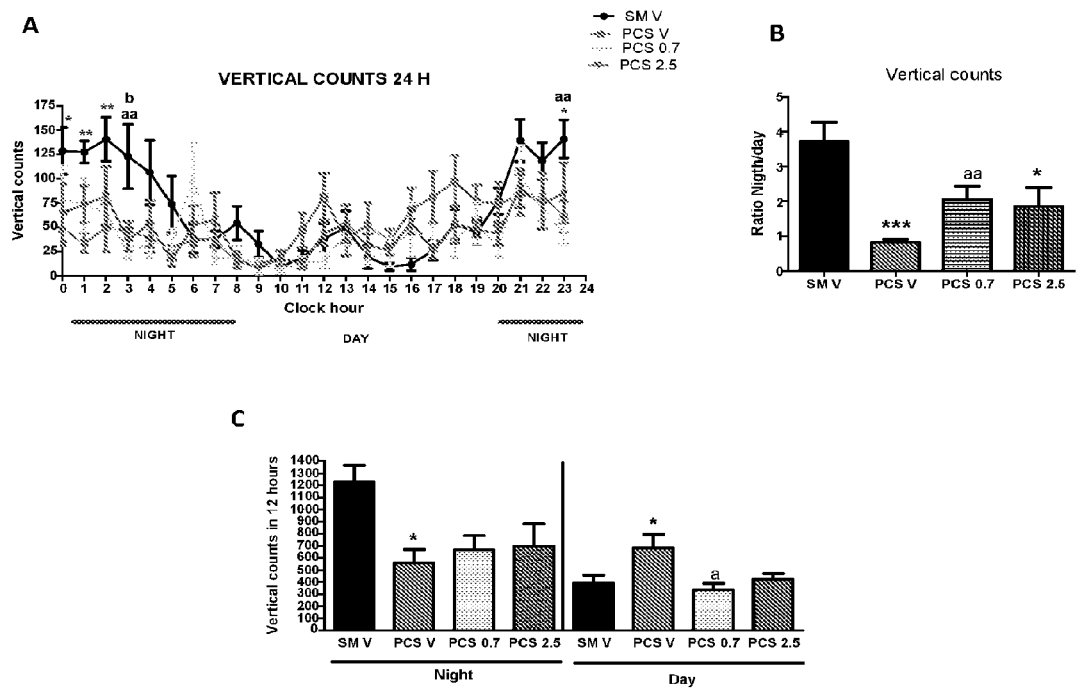

FIG. 13 illustrates the ability of 3α-ethynyl-3β-hydroxyandrostan-17-one oxime to normalize vertical activity during the day and to partially restore the circadian rhythm of PCS rats. The experiment was carried out as described for FIG. 12 but vertical counts are shown. Values are the mean±SEM of 8 rats per group. Values significantly different from SM rats are indicated by asterisks; * $p<0.05$; **

p<0.01; *** p<0.001. Values significantly different from PCS rats are indicated by a; a p<0.05; aa p<0.01.

Figure 14:
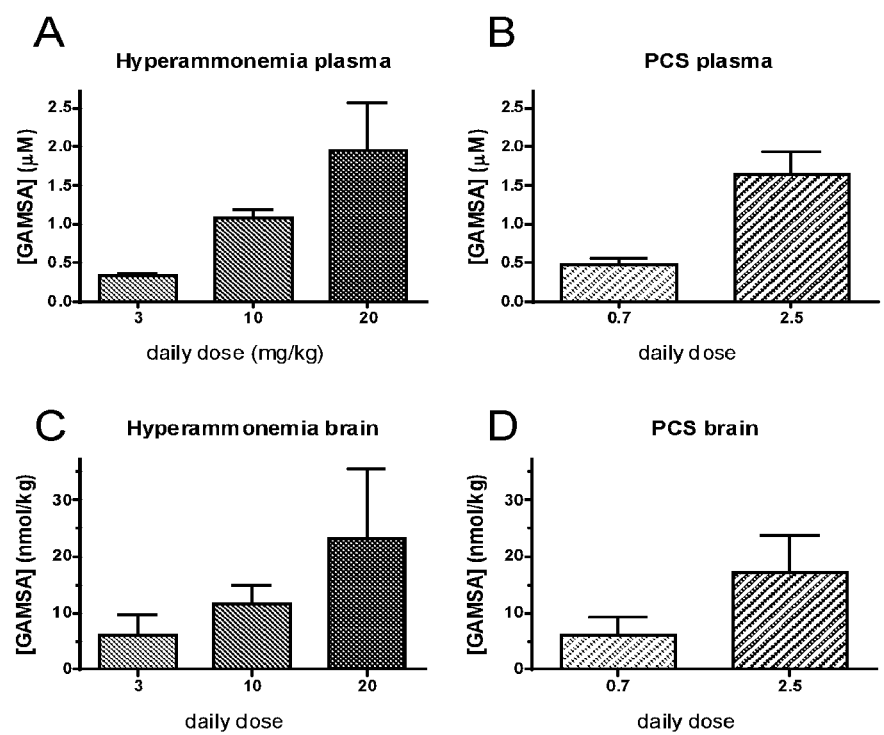

FIG. 14 shows 3α-ethynyl-3β-hydroxyandrostan-17-one oxime exposure in the plasma and in the brain at time at behavioral testing, in hyperammonemic and PCS rats. In A) hyperammonemic rats and B) PCS rats, the total plasma concentrations of 3α-ethynyl-3β-hydroxyandrostan-17-one oxime are shown in µM. In C) hyperammonemic rats and D) PCS rats, the unbound brain concentrations of 3α-ethynyl-3β-hydroxyandrostan-17-one oxime are shown in nmol/kg. Note the similar exposures in the different rat models with the doses used, in hyperammonemic rats 3, 10 and 20 mg/kg/day and in rats with PCS 0.7 and 2.5 mg/kg/day. Data are from the end of the study, i.e. after nine weeks of daily treatments with 3α-ethynyl-3β-hydroxyandrostan-17-one oxime in sesame oil given s.c. once daily.

Before the present invention is described in detail, it is to be understood that the terminology employed herein is used for the purpose of describing particular embodiments only and is not intended to be limiting.

It is noted that, as used in this specification and the appended claims, the singular forms "a", "an", and "the" also include plural referents unless the context clearly dictates otherwise.

The term "pharmaceutical composition" is used in its widest sense, encompassing all pharmaceutically applicable compositions containing at least one active substance and optional carriers, adjuvants, diluents, constituents etc.

The terms "administration" and "mode of administration" as well as "route of administration" are also used in their widest sense.

The compound 3α-ethynyl-3β-hydroxyandrostan-17-one oxime as used in accordance with the invention may be administered in a number of ways depending largely on whether a local, topical or systemic mode of administration is most appropriate for the hepatic encephalopathy condition to be treated. These different modes of administration are for example topical (e.g., on the skin), local (including ophthalmic and to various mucous membranes, for example vaginal and rectal delivery), oral, parenteral or pulmonary, including the upper and lower airways. The preparation of such compositions and formulations is generally known to those skilled in the pharmaceutical and formulation arts and may be applied to the formulation of the composition of the present invention.

With the term "antagonist" is meant a substance that hinders another substance, an agonist, to induce its effect. In this application the terms antagonist and blocker are used interchangeably.

With the term "Type A hepatic encephalopathy" is typically meant hepatic encephalopathy associated with acute liver failure, typically associated with cerebral oedema.

With the term "Type B hepatic encephalopathy" is typically meant hepatic encephalopathy (bypass) caused by portal-systemic shunting without associated intrinsic liver disease.

With the term "Type C hepatic encephalopathy" is typically meant hepatic encephalopathy occurring in patients with cirrhosis—this type is subdivided in episodic, persistent and minimal encephalopathy.

With the term "minimal hepatic encephalopathy" is typically meant hepatic encephalopathy that does not lead to clinically overt cognitive dysfunction, but can be demonstrated with neuropsychological studies.

With the term "overt hepatic encephalopathy" is typically meant clinically apparent hepatic encephalopathy manifested as neuropsychiatric syndrome with a large spectrum of mental and motor disorders. Overt hepatic encephalopathy may arise episodically, over a period of hours or days in patients previously stable or patients may present with persistent neuropsychiatric abnormalities.

With the term "hyperammonemia" is typically meant a metabolic disturbance characterized by an excess of ammonia in the blood.

With the term "liver transplantation" is typically meant a surgical procedure to remove a diseased liver as a consequence of e.g. acute liver failure or cirrhosis, and replace it with a healthy liver from a donor. Most liver transplant operations use livers from deceased donors but a liver may also come from a living donor (a portion of a healthy person's liver). Patients with e.g. cirrhosis commonly experience hepatic encephalopathy and preoperative hepatic encephalopathy is a significant predictor of post-transplant neurologic complications.

With the term "acute-on-chronic liver failure" is typically meant acute decompensation of cirrhosis, at least one organ failure, or belongs to a subgroup with high short-term mortality rate.

With the term "compensated cirrhosis" is typically meant liver cirrhosis without any clinical evidence but may include asymptotic esophageal or gastric varices and early symptoms such as fatigue and loss of energy, loss of appetite and weight loss, nausea or abdominal pain.

With the term "decompensated cirrhosis" is typically meant advanced liver cirrhosis with a range of clinical evidence such as jaundice, ascites, oedema, hepatic encephalopathy, gastrointestinal haemorrhage, portal hypertension, bacterial infections, or any combination.

With the term "portal hypertension" is typically meant a hepatic venous pressure gradient following liver cirrhosis, with or without associated transjugular intrahepatic portsystemic shunt (TIPS).

With the term "prevention" within this disclosure, is typically meant prevention of disease or disorder hepatic encephalopathy to occur.

With the term "alleviation" within this disclosure, is typically meant reduction of or freedom from the disease or disorder hepatic encephalopathy.

Patients suffering from hepatic encephalopathy may show symptoms including, but not limited to, impairments of the sleep-wake cycle, cognition, memory, learning, motor coordination, consciousness, decreased energy levels and personality change, cognitive impairment, disorientation and coma.

The present inventors have surprisingly shown that 3α-ethynyl-3β-hydroxyandrostan-17-one oxime may be useful for the treatment of hepatic encephalopathy.

In a first aspect of the invention, there is provided the compound 3α-ethynyl-3β-hydroxyandrostan-17-one oxime

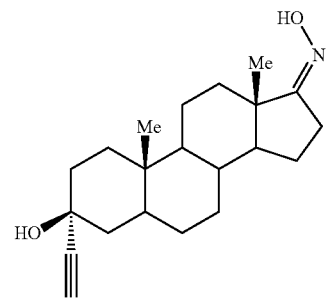 [SMILES: C#C[C@]1(O)CC[C@@]2(C)C(CCC3C2CC[C@]2(C)/C(=N\O)CCC32)C1]

or a pharmaceutically acceptable salt thereof, for use in treatment of hepatic encephalopathy.

In one embodiment of the invention, said hepatic encephalopathy is type A hepatic encephalopathy.

In another embodiment of the invention, said hepatic encephalopathy is type B hepatic encephalopathy.

In another embodiment of the invention, said hepatic encephalopathy is type C hepatic encephalopathy.

In another embodiment of the invention, said hepatic encephalopathy is minimal hepatic encephalopathy.

In another embodiment of the invention, said hepatic encephalopathy is overt hepatic encephalopathy.

In another embodiment of the invention, said compound for use is where said hepatic encephalopathy is treated in a patient with acute liver failure.

In another embodiment of the invention, said compound for use is where said hepatic encephalopathy is treated in a patient with chronic liver disease with or without acute-on-chronic liver failure.

In another embodiment of the invention, said compound for use is for prevention or alleviation of hepatic encephalopathy, such as type A hepatic encephalopathy, type B hepatic encephalopathy, type C hepatic encephalopathy, minimal hepatic encephalopathy, overt hepatic encephalopathy, in a patient with acute liver failure, or in a patient with chronic liver disease with or without acute-on-chronic liver failure.

In another embodiment of the invention, said compound for use is provided before, during or after a liver transplantation.

In another embodiment of the invention, there is provided a pharmaceutical composition comprising 3α-ethynyl-3β-hydroxyandrostan-17-one oxime or a pharmaceutically acceptable salt thereof, for use in treatment of hepatic encephalopathy, together with one or more pharmaceutically acceptable carriers, excipients and/or diluents.

In another aspect of the invention, there is provided a method of treating hepatic encephalopathy, comprising administering a pharmaceutically effective amount of 3α-ethynyl-3β-hydroxyandrostan-17-one oxime

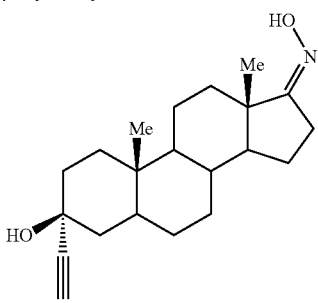

or a pharmaceutically acceptable salt thereof, to a patient in need thereof.

In one embodiment of the invention, said hepatic encephalopathy is type A hepatic encephalopathy.

In another embodiment of the invention, said hepatic encephalopathy is type B hepatic encephalopathy.

In another embodiment of the invention, said hepatic encephalopathy is type C hepatic encephalopathy.

In another embodiment of the invention, said hepatic encephalopathy is minimal hepatic encephalopathy.

In another embodiment of the invention, said hepatic encephalopathy is overt hepatic encephalopathy.

In another embodiment of the invention, said patient suffers from acute liver failure.

In another embodiment of the invention, said patient suffers from chronic liver disease with or without acute-on-chronic liver failure.

In another embodiment of the invention, said compound is provided before, during or after a liver transplantation.

In another embodiment of the invention, there is provided a method of preventing or alleviating hepatic encephalopathy, comprising administering a pharmaceutically effective amount of 3α-ethynyl-3β-hydroxyandrostan-17-one oxime

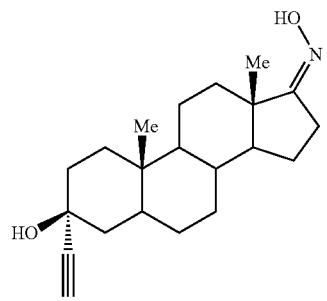 [SMILES: C#C[C@]1(O)CC[C@@]2(C)C(CCC3C2CC[C@]2(C)/C(=N\O)CCC32)C1]

or a pharmaceutically acceptable salt thereof, to a patient in need thereof. Said hepatic encephalopathy may be type A hepatic encephalopathy, type B hepatic encephalopathy, type C hepatic encephalopathy, minimal hepatic encephalopathy or overt hepatic encephalopathy. Further, said prevention may be in a patient with acute liver failure, or in a patient with chronic liver disease with or without acute-on-chronic liver failure.

In a another aspect of the invention, there is provided the compound 3α-ethynyl-3β-hydroxyandrostan-17-one oxime

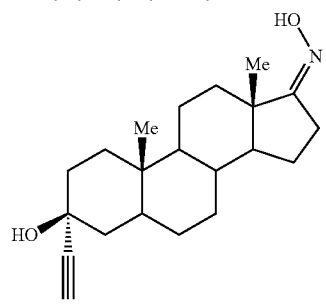 [SMILES: C#C[C@]1(O)CC[C@@]2(C)C(CCC3C2CC[C@]2(C)/C(=N\O)CCC32)C1]

or a pharmaceutically acceptable salt thereof, for use in treatment of portal hypertension. Said use may also be prevention or alleviation of portal hypertension. The patient with portal hypertension typically suffers from a liver disease, such as a chronic liver disease, cirrhosis or acute liver failure.

In another aspect of the invention, there is provided a method of treating portal hypertension, comprising administering a pharmaceutically effective amount of 3α-ethynyl-3β-hydroxyandrostan-17-one oxime

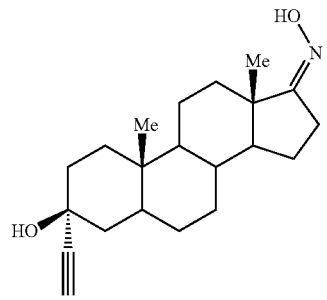 [SMILES: C#C[C@]1(O)CC[C@@]2(C)C(CCC3C2CC[C@]2(C)/C(=N\O)CCC32)C1]

or a pharmaceutically acceptable salt thereof, to a patient in need thereof. Said method may also be in prevention or alleviation of portal hypertension. The patient with portal hypertension typically suffers from a liver disease, such as a chronic liver disease, cirrhosis or acute liver failure.

In a another aspect of the invention, there is provided the compound 3α-ethynyl-3β-hydroxyandrostan-17-one oxime

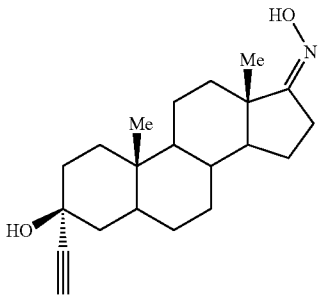 [SMILES: C#C[C@]1(O)CC[C@@]2(C)C(CCC3C2CC[C@]2(C)/C(=N\O)CCC32)C1]

or a pharmaceutically acceptable salt thereof, for use in treatment of liver decompensation. Said use may also be prevention or alleviation of liver decompensation. The patient with liver decompensation typically suffers from a liver disease, such as a chronic liver disease or may be suspected of having a precipitating event, such as gastrointestinal bleeding, infection, portal vein thrombosis or dehydration.

In another aspect of the invention, there is provided a method of treating liver decompensation, comprising administering a pharmaceutically effective amount of 3α-ethynyl-3β-hydroxyandrostan-17-one oxime

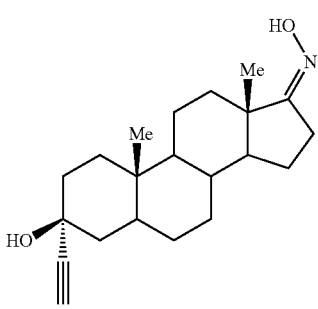 [SMILES: C#C[C@]1(O)CC[C@@]2(C)C(CCC3C2CC[C@]2(C)/C(=N\O)CCC32)C1]

or a pharmaceutically acceptable salt thereof, to a patient in need thereof. Said method may also be in prevention or alleviation of liver decompensation. The patient with liver decompensation typically suffers from a liver disease, such as a chronic liver disease or may be suspected of having a precipitating event, such as gastrointestinal bleeding, infection, portal vein thrombosis or dehydration.

In a another aspect of the invention, there is provided use of the compound 3α-ethynyl-3β-hydroxyandrostan-17-one oxime

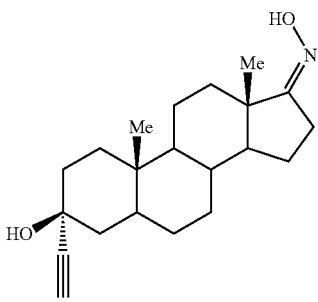 [SMILES: C#C[C@]1(O)CC[C@@]2(C)C(CCC3C2CC[C@]2(C)/C(=N\O)CCC32)C1]

or a pharmaceutically acceptable salt thereof, in the manufacture of a medicament for treating hepatic encephalopathy.

In one embodiment of the invention, said hepatic encephalopathy is type A hepatic encephalopathy.

In another embodiment of the invention, said hepatic encephalopathy is type B hepatic encephalopathy.

In another embodiment of the invention, said hepatic encephalopathy is type C hepatic encephalopathy.

In another embodiment of the invention, said hepatic encephalopathy is minimal hepatic encephalopathy.

In another embodiment of the invention, said hepatic encephalopathy is overt hepatic encephalopathy.

In another embodiment of the invention, said use is where said hepatic encephalopathy is treated in a patient with acute liver failure.

In another embodiment of the invention, said use is where said hepatic encephalopathy is treated in a patient with chronic liver disease with or without acute-on-chronic liver failure.

In another embodiment of the invention, said use is provided before, during or after a liver transplantation.

In another embodiment of the invention, said use of the compound 3α-ethynyl-3-β-hydroxyandrostan-17-one oxime, or a pharmaceutically acceptable salt thereof, in the manufacture of a medicament, may be for prevention or alleviation of hepatic encephalopathy, such as type A hepatic encephalopathy, type B hepatic encephalopathy, type C hepatic encephalopathy, minimal hepatic encephalopathy, overt hepatic encephalopathy, in a patient with acute liver failure, or in a patient with chronic liver disease with or without acute-on-chronic liver failure.

In another embodiment of this aspect, there is provided a pharmaceutical composition comprising 3α-ethynyl-3β-hydroxyandrostan-17-one oxime or a pharmaceutically acceptable salt thereof, for use in treatment of hepatic encephalopathy, together with pharmaceutically acceptable carriers, excipients and or diluents. Said use may also be in prevention or alleviation of hepatic encephalopathy.

In further aspect of the invention, is the compound 3α-ethynyl-3β-hydroxyandrostan-17-one oxime

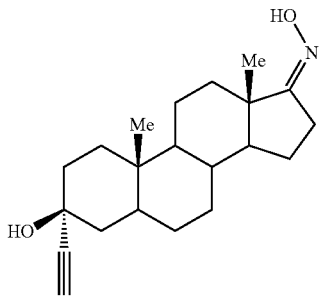 [SMILES: C#C[C@]1(O)CC[C@@]2(C)C(CCC3C2CC[C@]2(C)/C(=N\O)CCC32)C1]

or a pharmaceutically acceptable salt thereof for use in inhibiting or treating symptoms caused by hyperammonemia.

A further embodiment of the invention is the compound 3α-ethynyl-3β-hydroxyandrostan-17-one oxime for use in the treatment or prevention of hepatic encephalopathy, such as type A hepatic encephalopathy, type B hepatic encephalopathy, type C hepatic encephalopathy, minimal hepatic encephalopathy, overt hepatic encephalopathy, in a patient with acute liver failure, or in a patient with chronic liver disease with or without acute-on-chronic liver failure; wherein said treatment or prevention comprises the co-administration of 3α-ethynyl-3β-hydroxyandrostan-17-one oxime, or a pharmaceutically acceptable salt thereof, with an ammonia-lowering compound, such as rifaximin, lactulose, ornithine phenylacetate and glycerol phenylbutyrate, preferably the ammonia-lowering compound is rifaximin or lactulose, and most preferably the ammonia-lowering compound is rifaximin.

A further embodiment of the invention is a method of treatment or prevention of hepatic encephalopathy, such as type A hepatic encephalopathy, type B hepatic encephalopathy, type C hepatic encephalopathy, minimal hepatic encephalopathy, overt hepatic encephalopathy, in a patient with acute liver failure, or in a patient with chronic liver disease with or without acute-on-chronic liver failure; wherein said treatment or prevention comprises the co-administration of 3α-ethynyl-3β-hydroxyandrostan-17-one oxime, or a pharmaceutically acceptable salt thereof, with an ammonia-lowering compound, such as rifaximin, lactulose, ornithine phenylacetate and glycerol phenylbutyrate, preferably the ammonia-lowering compound is rifaximin or lactulose, and most preferably the ammonia-lowering compound is rifaximin.

A further embodiment of the invention is the use of the compound 3α-ethynyl-3β-hydroxyandrostan-17-one oxime in the manufacture of a medicament for the treatment or prevention of hepatic encephalopathy, such as type A hepatic encephalopathy, type B hepatic encephalopathy, type C hepatic encephalopathy, minimal hepatic encephalopathy, overt hepatic encephalopathy, in a patient with acute liver failure, or in a patient with chronic liver disease with or without acute-on-chronic liver failure; wherein said treatment or prevention comprises the co-administration of 3α-ethynyl-3β-hydroxyandrostan-17-one oxime, or a pharmaceutically acceptable salt thereof, with an ammonia-lowering compound, such as rifaximin, lactulose, ornithine phenylacetate and glycerol phenylbutyrate, preferably the ammonia-lowering compound is rifaximin or lactulose, and most preferably the ammonia-lowering compound is rifaximin.

A further aspect of the invention is the compound 3α-ethynyl-3β-hydroxyandrostan-17-one oxime, wherein one or more hydrogen atom in each possible substituent position may be substituted for deuterium or tritium, for use in the treatment of hepatic encephalopathy such as minimal hepatic encephalopathy or overt hepatic encephalopathy.

A further aspect of the invention is the compound 3α-ethynyl-3β-hydroxyandrostan-17-one oxime, wherein one or more hydrogen atom in each possible substituent position may be substituted for deuterium or tritium, for use assays that involve determining the concentration of the compound in tissue or fluids.

According to the present invention, 3α-ethynyl-3β-hydroxyandrostan-17-one oxime may be administered through one of the following routes of administration: intravenously, nasally, per rectum, bucally, intravaginally, percutaneously, intramuscularly and orally. According to one embodiment, 3α-ethynyl-3β-hydroxyandrostan-17-one oxime is administered intravenously. According to another embodiment, 3α-ethynyl-3β-hydroxyandrostan-17-one oxime is administered nasally. Percutaneous administration, using 3α-ethynyl-3β-hydroxyandrostan-17-one oxime formulated as a cream, a gel, and an ointment or in the form of slow-release adhesive medicine patches, is another possible form of administration, similarly suitable for self-medication.

The pharmaceutical composition may be adapted or adjusted according to normal pharmacological procedures, comprising the effective pharmaceutical in a chemical form, suitable for the chosen route, together with suitable adjuvants, carriers, diluents and vehicles, conventionally used and well-known to a person skilled in the art. Conventionally used adjuvants and vehicles for oral administration are for example fillers or suspending agents like titanium dioxide, lactose anhydride, silica, silica colloidalis, methylcellulose, magnesium stearate, microcrystalline cellulose and the like. Conventionally used adjuvants and vehicles for intravenous administration are for example sterile water for injections (WFI), sterile buffers (for example buffering the solution to pH 7.4) albumin solution, lipid solutions, cyclodextrins and the like. Conventionally used adjuvants and vehicles for transdermal administration are for example Vaseline, liquid paraffin, glycerol, water, MCT oil, sesame oil, vegetable oils and the like. The dose will naturally vary depending on the mode of administration, the particular condition to be treated or the effect desired, gender, age, weight and health of the patient, as well as possibly other factors, evaluated by the treating physician.

The invention will now be described by a number of illustrative, non-limiting examples.

Example 1

Synthesis of
3α-ethynyl-3β-hydroxyandrostan-17-one oxime

Step 1: Synthesis of
3α-ethynyl-3β-hydroxyandrostan-17-one 3,17-androstandione (5.0 mmol) was dissolved in 50 mL dry THF at room temperature (rt) under nitrogen. Ethynyl magnesium bromide (1.1 equiv) was added dropwise at rt under stirring and the solution was left stirring overnight at rt under nitrogen flow. The solution was then quenched with saturated $NH_4Cl_{(aq)}$ and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether:dichloromethane), typical yields 65%. Eventual traces of byproducts can be eliminated by further recrystallization from diethylether. $^1$H NMR (400 MHz, $CDCl_3$-$d_6$): δ 2.43 (s, 1H); 2.42 (m, 1H); 2.10-2.04 (m, 2H); 1.02 (m, 1H); 0.86 (s, 3H); 0.83 (s, 3H).

Step 2: Synthesis of
3α-ethynyl-3β-hydroxyandrostan-17-one oxime

3α-ethynyl-3β-hydroxyandrostan-17-one (10 mmol) was dissolved in dichloromethane 5 mL and ethanol 50 mL at room temperature and air atmosphere, in a 250 mL round bottom flask. 4 equiv. of $NH_2OH$ hydrochloride and 4 equiv. of sodium acetate were dissolved in 5 mL $H_2O$ and then added to the steroid solution. 20 mL of ethanol was added and the mixture put on reflux overnight. The mixture was then cooled and the solvent removed under reduced pressure. The white residue was treated with 50 mL $H_2O$ and 50 mL dichloromethane, the aqueous phase extracted with 3×30 mL dichloromethane. The collected organic phases were then dried over $MgSO_4$, filtrated and the solvent removed under reduced pressure. The final residue was purified by silica flash column chromatography dichloromethane:diethyl ether 4:1, typical yields 95-100% (quantitative).

$^1$H NMR (400 MHz, CDCl$_3$-d$_6$): δ 2.51-2.47 (m, 2H); 2.43 (s, 1H); 1.00 (m, 1H); 0.80 (m, 1H); 0.90 (s, 3H), 0.83 (s, 3H).

Example 2

Therapeutic Effect of
3α-Ethynyl-3β-Hydroxyandrostan-17-One Oxime in
Animal Model of Hepatic Encephalopathy Treatment and Testing Schedule In this study an animal model of chronic hyperammonemia was used that reproduces many of the cognitive and motor alterations present in hepatic encephalopathy. Rats were fed with ammonia in their food and after two weeks with ammonia enriched food they developed symptoms of hepatic encephalopathy. The beam walking test was made during the 3$^{rd}$ and 4$^{th}$ week of 3α-ethynyl-3β-hydroxyandrostan-17-one oxime treatment while the Morris Water maze test was made during 4$^{th}$-5$^{th}$ week of 3α-ethynyl-3β-hydroxyandrostan-17-one oxime treatment and the Radial maze test was made during 6$^{th}$-7$^{th}$ week of 3α-ethynyl-3β-hydroxyandrostan-17-one oxime treatment.

The study was divided into two series with animals (male Wistar rats), each series included the following groups; Controls treated with vehicle (CV, n=8 per series), Controls treated with 3α-ethynyl-3β-hydroxyandrostan-17-one oxime (C+GAM, n=8 per series), hyperammonemic rats treated with vehicle (HAV, n=8 per series), hyperammonemic rats treated with 3α-ethynyl-3β-hydroxyandrostan-17-one oxime (HA+GAM, n=8 per series). The once daily treatment with 3α-ethynyl-3β-hydroxyandrostan-17-one oxime at 20 mg/kg or with vehicle was performed with subcutaneous injections of 1 ml/kg around 9 a.m. Treatment started one week after starting with the ammonium containing diet and continued for the whole experimental period.

Test article of 3α-ethynyl-3β-hydroxyandrostan-17-one oxime was prepared as a suspension in sesame oil at 20 mg/kg.

Spatial Learning in the Radial Maze

The Radial maze was designed as a method to assess spatial learning. The apparatus is composed of a central area that gives access to eight equally-sized arms. The arms were 70 cm long and 10 cm wide and the central area was 30 cm in diameter. The maze was made of black Perspex and was elevated 80 cm above de floor. Each arm had lateral walls with a height higher in the side proximal to the central area (30 cm) than in the distal side (5 cm). In the distal extreme of each arm, a recessed cup was installed for positioning the food rewards (Hernandez-Rabaza V. et al 2010).

To habituate rats to the maze, the rats were allowed to explore the maze for 10 minutes on two consecutive days in the presence of distal cues (posters and objects of different sizes), which remained in place throughout training.

Training in the radial maze was composed of five blocks of three trials each, performed on ten consecutive days. The task involved locating four pellets, each placed at the end of a different arm according to a random configuration. Configurations were specific for each rat and were kept invariable throughout training. The number of spatial reference errors and working memory were calculated and expressed as number of reference and working errors per block. In addition, a learning index was used to evaluate the learning of the task and was defined as number of right choices-reference errors (Hernandez-Rabaza et al. 2010).

Results

Figure 2:
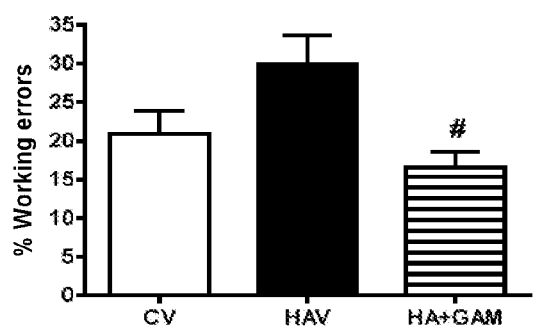
FIG. 2 shows that 3α-ethynyl-3β-hydroxyandrostan-17-one oxime restores spatial learning of hyperammonemic rats in the Radial maze. The figure shows working errors in the radial test. Working errors in block 1. Values are the mean±SEM of 8 rats per group. # p<0.05 versus HAV. CV=control rats treated with vehicle; HAV= hyperammonemic rats treated with vehicle; HA+GAM= hyperammonemic rats treated with 3α-ethynyl-3β-hydroxyandrostan-17-one oxime.

3α-ethynyl-3β-hydroxyandrostan-17-one oxime restored spatial learning of hyperammonemic rats in the Radial maze. Hyperammonemic rats show reduced spatial learning and perform more working errors in the Radial maze task. Spatial memory was completely restored by 3α-ethynyl-3β-hydroxyandrostan-17-one oxime (FIG. 2).

Example 3

Therapeutic Effect of
3α-Ethynyl-3β-Hydroxyandrostan-17-One Oxime in
Animal Model of Hepatic Encephalopathy Treatment and Testing Schedule The treatment and testing schedule was as set out in example 2.

Spatial Memory in the Morris Water Maze

The maze was designed as a method to assess spatial learning (Morris R. 1984). The test was carried out using a black circular pool (160 cm diameter, 40 cm height) arbitrarily divided into four quadrants. Water opacity was obtained by adding black paint. A transparent Plexiglas platform, 10 cm in diameter, was immersed 2 cm under the water surface at the centre of one quadrant during training sessions (Monfort et al., *European Journal of Neuroscience*, 2007, 25, 2103-211).

The test was carried out as follows; the first day was the pre-training day, rats were put in the water two times for 30 s only to adapt to water. Then the rats were trained to learn the fixed location of the invisible platform during 3 days. Each training trial involved placing the rat into the pool facing the wall at one of the three quadrants lacking the platform. A different starting point was randomly used on each trial. Training consisted of five swims per day. Each animal was allowed a maximum of 120 s to find the platform and was left for 15 s on the platform, if a rat failed to locate the platform within 120 s it was manually guided to the platform by the experimenter. The aim of this test is that the rats learn where the invisible platform is placed and reach it in the shortest time possible. The time, speed and path needed to find the hidden platform was recorded by a video tracking system provided by Viewpoint Company (Viewpoint 2.5, Champagne au Mont D' Or, France) and used as a measure of learning of the task. After 15 training trial, the platform was removed from the pool, the rats were allowed to swim for 90 s in the pool and the time spent in the quadrant where the platform was positioned during training was recorded.

Results

3α-ethynyl-3β-hydroxyandrostan-17-one oxime completely restored spatial memory of hyperammonemic rats in the Morris water maze. Hyperammonemic rats showed reduced memory and needed more time than controls to find the platform (FIG. 3).

Example 4

Therapeutic Effect of
3α-Ethynyl-3β-Hydroxyandrostan-17-One Oxime in
Animal Model of Hepatic Encephalopathy Treatment and Testing Schedule The treatment and testing schedule was as set out in example 2.

Motor Coordination in the Beam Walking

In the beam-walking test rats are trained to traverse an elevated, narrow beam to reach an enclosed escape platform.

The beam is made of smooth round wood (20 mm in diameter). The beam is elevated 1 m from the floor. The parameters of motor coordination measured are: footslips (or foot faults) and latency to traverse the beam. (Jover et al., 2006; Carter et al., 2010). To habituate the rat, the experimenter places the rat at the beginning of the beam and helps the rat to cross the beam three times. After that, the test consists of three consecutive trials. The number of times the left or right hind paw slip off the beam was recorded for each trial.

Results

3α-ethynyl-3β-hydroxyandrostan-17-one oxime completely reversed motor in-coordination of hyperammonemic rats in the beam-walking test. Hyperammonemic rats showed motor in-coordination (increased number of slips=foot faults) (FIG. 4).

Example 5

Concentrations of
3α-Ethynyl-3β-Hydroxyandrostan-17-One Oxime in Plasma and Brain Tissue after Exogenous Administration Obtaining Plasma Blood was obtained from the tail of the rats (from Example 2) in the end of second week of ammonia treatment and first week of 3α-ethynyl-3β-hydroxyandrostan-17-one oxime treatment and also from the neck during the animal sacrifice. To obtain the plasma it was added EDTA 7.5 nM and centrifuged at 1500 r.p.m during 5 minutes.

Ammonia Determination

Ammonia concentration in blood samples was measured using the Pocket chem BA (Woodley Equipment Company Ltd, United Kingdom), an ammonia analyzer. The device enables immediate testing and delivers results in 3 minutes and 20 s. It also eliminates the need for pre-processes such as centrifugal separation.

Sacrifice

Rats were sacrificed by decapitation. One half of the brain including the cerebellum was collected and conserved at −80° C. for determination of 3α-ethynyl-3β-hydroxyandrostan-17-one oxime. Different brain areas (cerebellum, cortex, hippocampus and striatum) were dissected and conserved at −80° C. for possible determination of GAMS.

Analysis of
3α-ethynyl-3β-hydroxyandrostan-17-one oxime concentration

Collected brain and plasma samples were analyzed for 3α-ethynyl-3β-hydroxyandrostan-17-one oxime concentrations. Plasma and brain samples were thawed at room temperature. Plasma was protein-precipitated with a 3-fold volume with acetonitrile and brain tissue was homogenized with a 1:4 ratio of tissue:PBS (pH 7.4) and then extracted with a 2-fold volume of methanol:acetonitrile (1:1) for 20 min during sonication. Thereafter samples were shaken and centrifuged for 10 min at 10 000×g (Heraeus Pico 17 centrifuge). The supernatant was then diluted with an equal volume of PBS and analyzed. Some samples were reanalyzed as 10-fold dilutions due to too high concentration of 3α-ethynyl-3β-hydroxyandrostan-17-one oxime. The dilutions were made with a solution of 37.5% acetonitrile in PBS buffer.

Standards were prepared by spiking blank plasma/brain homogenate into the concentrations 0.5-5 000 ng/ml and otherwise treated as the samples. The determination was made with LC-MS.

Results

Figure 1:
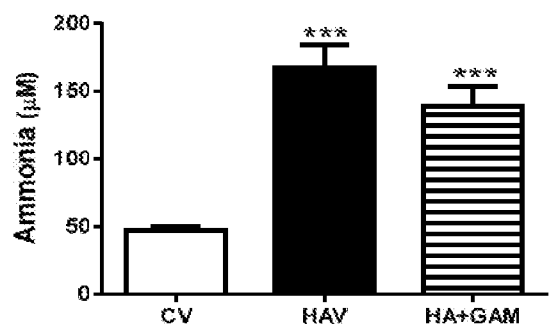
FIG. 1 shows that 3α-ethynyl-3β-hydroxyandrostan-17-one oxime does not affect blood ammonia levels. Values are the mean±SEM of 12 rats per group, values significantly different from controls are indicated by asterisks; ***, p<0.001. CV=control rats treated with vehicle; HAV= hyperammonemic rats treated with vehicle; HA+GAM= hyperammonemic rats treated with 3α-ethynyl-3β-hydroxyandrostan-17-one oxime.

Ammonia determination: 3α-ethynyl-3β-hydroxyandrostan-17-one oxime did not affect blood ammonia levels. Ammonia levels in blood are increased in rats fed the ammonium diet (167±17 μM) compared to control rats (47±3 μM). 3α-ethynyl-3β-hydroxyandrostan-17-one oxime did not affect blood ammonia levels in control rats (55±7 μM) or in hyperammonemic rats (139±15 μM) (FIG. 1). These results are surprising as all earlier studies showing effect on hepatic encephalopathy symptoms have decreased ammonia levels.

Determination of 3α-Ethynyl-3β-Hydroxyandrostan-17-One Oxime after Exposure

In the present study the total concentration of 3α-ethynyl-3β-hydroxyandrostan-17-one oxime in plasma was analysed on treatment day five and at the last week of treatment with 3α-ethynyl-3β-hydroxyandrostan-17-one oxime, four hours and 23 hours after injection, respectively. The concentrations of 3α-ethynyl-3β-hydroxy, androstan-17-one oxime in plasma are shown in FIG. 5 and the brain concentrations in FIG. 6. On treatment day five the concentrations of 3α-ethynyl-3β-hydroxyandrostan-17-one oxime were lower 23 hours after injection than 4 hours after injection, while at the last week of treatment similar concentrations of 3α-ethynyl-3β-hydroxyandrostan-17-one oxime were found at both 4 hours and 23 hours in both groups, respectively. In the brain, similar concentrations of 3α-ethynyl-3β-hydroxyandrostan-17-one oxime were found in control (91±4.1 nmol/kg unbound* 3α-ethynyl-3β-hydroxyandrostan-17-one oxime) and in HA rats (106±15.4 nmol/kg unbound* 3α-ethynyl-3β-hydroxyandrostan-17-one oxime), 1-2 h after the last treatment (FIG. 6). The concentrations showed surprising high levels and stable concentrations throughout the 24 hours.

*Unbound brain concentration=fraction of 3α-ethynyl-3β-hydroxyandrostan-17-one oxime in the brain that is not bound to carrier protein or brain tissue.

Example 6

Ability of
3α-Ethynyl-3β-Hydroxyandrostan-17-One Oxime to Antagonize the Effect of THDOC but not GABA at the $GABA_A$ Receptor Whole-Cell Voltage-Clamp Electrophysiology with α1β2γ2L and α5β3γ2L $GABA_A$ Receptors For electrophysiology measurements the Dynaflow® system with the Resolve chip was used (Cellectricon, Göteborg, Sweden). HEK-293 cells were permanently transfected with vectors including the human CMV promoter for constitutive expression of the human α5, β3, and γ2L $GABA_A$ receptor subunits (α5β3γ2L) or the human α1, β2, and γ2L $GABA_A$ receptor subunits (α1β2γ2L). The cell lines used were selected for good reactivity to GABA and to THDOC. Before measurements cells were incubated for 15 min at 37° C. in 95% air+5% $CO_2$ in extracellular solution (EC) containing the following: 137 mM NaCl, 5.0 mM KCl, 1.0 mM $CaCl_2$, 1.2 mM $MgCl_2$, 10 mM HEPES, and 10 mM glucose, 0.1% DMSO pH 7.4. Thereafter, detached cells were added to the EC solution in the Dynaflow chip bath.

Whole-cell voltage-clamp recordings were made at room temperature (21-23° C., −17 mV with compensation for liquid junction potential as in Haage et al., 2002; Neher, 1992). Command pulses were generate and data collected by PClamp 9.0 software, DigiData 1322A converter, and Axon-Patch 200B (Axon Instruments, Foster City, Calif.). Patch electrodes (2-6 MΩ) were filled with intracellular solution (IC) including: 140 mM Cs-gluconate, 3.0 mM NaCl, 1.2 mM MgCl$_2$, 10 mM HEPES, 1.0 mM EGTA, 2 mM Mg-ATP, 0.1% DMSO, pH 7.2.

THDOC and 3α-ethynyl-3β-hydroxyandrostan-17-one oxime were dissolved in dimethyl sulfoxide (DMSO) and thereafter diluted with EC solution to include 0.1% DMSO.

Different protocols were used for different electrophysiology measurements. As α1β2γ2L-GABA$_A$ receptors in vivo are present within the synapse a condition resembling that situation, a short application (40 ms) of a high GABA concentration (30 µM), was used. Contrary, α5β3γ2L-GABA$_A$ receptors are present extrasynaptically, thus the conditions used were long exposures (6 s) to a low GABA concentration (0.3 µM). The EC$_{75}$ concentration of THDOC was used, i.e. 100 nM with studies of α1β2γ2L and 200 nM when α5β3γ2L expressing cells were evaluated. With both cell types a pre-exposure with THDOC or THDOC plus 3α-ethynyl-3β-hydroxyandrostan-17-one oxime was used before application of GABA.

Steroid effects in presence of GABA were normalized to controls in order to avoid the effects of inter- and intracellular variation in the measured parameters, each cell was used as its own control and the area under the curve (AUC) was analyzed.

Results

The effects of 3α-ethynyl-3β-hydroxyandrostan-17-one oxime at the GABA$_A$ receptor were studied with electrophysiological measurements on recombinant HEK293-cells expressing human variants of the receptor. The 100 nM THDOC-enhanced activation of the α1β2γ2L GABA$_A$ receptor in presence of GABA is shown in FIG. 7.

3α-Ethynyl-3β-hydroxyandrostan-17-one oxime (1 µM) partly antagonises the effect of THDOC at both the α1β2γ2L and the α5β3γ2L subunit variants of the GABA$_A$ receptor (FIGS. 8 A and C). With α1β2γ2L receptors 3α-ethynyl-3β-hydroxyandrostan-17-one oxime inhibits 29±4.7% of the THDOC enhancement of GABA (P<0.001) and with the α5β3γ2L receptor the inhibition is 49±4.7% (P<0.001, Table 1).

Contrary, 3α-ethynyl-3β-hydroxyandrostan-17-one oxime (1 µM) does not antagonize the GABA-activation of the GABA$_A$ receptor (FIGS. 8 B and D). There is no significant effect of 3α-ethynyl-3β-hydroxyandrostan-17-one oxime at either the α1β2γ2L GABA$_A$ receptor (−3.1±1.7%, NS) or the α5β3γ2L GABA$_A$ receptor (−3.8±1.5%, NS) when GABA is the sole activator of the receptor (Table 1).

TABLE 1

Ability of 3α-ethynyl-3β-hydroxyandrostan-17-one (GAMSA) to antagonize THDOC but not GABA at the GABA$_A$ receptor.

| GABA$_A$ receptor | [GAMSA] µM | [GABA] µM | [THDOC] nM | GAMSA effect | P-value |
|---|---|---|---|---|---|
| α1β2γ2L | 1 | 30 | 100 | −29 ± 4.7% | <0.001 |
|  | 1 | 30 | — | −3.1 ± 1.7% | >0.05, NS |
| α5β3γ2L | 1 | 0.3 | 200 | −49 ± 4.7% | <0.001 |
|  | 1 | 0.3 | — | −3.8 ± 1.5% | >0.05, NS |

Example 7

Selectivity of 3α-Ethynyl-3β-Hydroxyandrostan-17-One Oxime Over Other Targets and Receptors The binding of 3α-ethynyl-3β-hydroxyandrostan-17-one oxime was determined for receptors, ion channels and enzymes, including all major classes of neurotransmitter receptors. In total 113 targets were tested in duplicate with 3α-ethynyl-3β-hydroxyandrostan-17-one oxime at 10 µM (Perkin Elmer, Customized screen). Binding activity was defined as greater than or equal to 50% inhibition of ligand binding.

Results

At 10 µM 3α-ethynyl-3β-hydroxyandrostan-17-one oxime did not show binding activity at any of the studied neurotransmitter related receptors, steroid receptors, or peptide receptors.

Example 8

Therapeutic Effect of 3α-Ethynyl-3β-Hydroxyandrostan-17-One Oxime on the Motor Co-Ordination of Rats with HE and Porta-Caval Anastomosis Treatment and Testing Schedule
Chronic Hyperammonemia in Rats.

Male Wistar rats (140-160 g) were made hyperammonemic by feeding them a diet containing ammonium acetate (30% by weight) (Felipo et al, *European Journal of Biochemistry*, 1988, 176, 567-571).

Porta-Caval Anastomosis.

Male Wistar rats (220-240 g) were anesthetized with isoflurane, and an end-to side porta-caval anastomosis was performed as described by Lee and Fisher (*Surgery*, 1961, 50, 668-672). Control rats were sham operated; they had the portal vein and inferior vena cava clamped for 10 min.

Rats that were subjected to the porta-caval anastomosis procedure are herein referred to as "PCS rats".

Adequate measures were taken to minimize pain and discomfort to the animals. The experiments were approved by the Comite de Experimentación y Bienestar Animal (CEBA) of our Center and were performed in accordance with guidelines of the Directive of the European Commission (2010/63/EU) and Spanish legislation (R.D. 1201/2005 for care and management of experimental animals.

Treatment with 3α-Ethynyl-3β-Hydroxyandrostan-17-One Oxime.

3α-ethynyl-3β-hydroxyandrostan-17-one oxime in sesame oil was administered by subcutaneous injections in the back of the rats, once daily. Two different sets of experiments were performed in hyperammonemic rats. In the first set four groups of rats were used: 1) control rats injected with vehicle; 2) hyperammonemic rats injected with vehicle; 3) control rats injected with 20 mg/Kg of 3α-ethynyl-3β-hydroxyandrostan-17-one oxime and 4) hyperammonemic rats injected with 20 mg/Kg of 3α-ethynyl-3β-hydroxyandrostan-17-one oxime.

Control rats injected with 3α-ethynyl-3β-hydroxyandrostan-17-one oxime were not included thereafter because no relevant effect was found in these rats.

In the second set of experiments five groups of rats were used: 1) control rats injected with vehicle; 2) hyperammonemiac rats injected with vehicle and 3-5) hyperammonemic rats injected with 3, 10 or 20 mg/Kg of 3α-ethynyl-3β-hydroxyandrostan-17-one oxime. In each experiment 6-8 rats per group were used.

For the experiments using PCS rats, the following groups of rats were used: 1) Sham rats injected with vehicle; 2) PCS rats injected with vehicle; 3-4) PCS rats injected with 0.7 or 2.5 mg/Kg of 3α-ethynyl-3β-hydroxyandrostan-17-one oxime. The number of rats used in each experiment is either shown in the corresponding Figure or given in the description of the corresponding Figure.

Statistical Analysis.

The data shown are the mean±SEM of the number of rats indicated in each Figure. Statistical significance was estimated with two-way ANOVA and Bonferroni post-test and with Student's t-test when only one parameter was compared. The analyses were performed using GraphPad PRISM software for Windows (GraphPad software Inc., La Jolla, Calif., USA).

Motor Coordination. Beam Walking Test.

Motor coordination was tested as described by Gonzalez-Usano et al (ACS Chemical Neuroscience, 2014, 19, 5(2), 100-105) using a wooden beam (20 mm diameter). Rats were made to traverse a one-meter-long wooden beam located approximately one meter above the ground, and the number of foot faults (slips) was recorded by two observers. The rats were trained for the test by being made to traverse the beam up to five times before measurements were recorded. The number of foot faults (slips) is a measure of motor in-coordination.

Results

3α-Ethynyl-3β-hydroxyandrostan-17-one oxime was shown to restore motor coordination for both the hyperammonemic and PCS rats.

Hyperammonemic rats show motor in-coordination in the beam walking test, with higher (p<0.05) number of slips (1.4±0.1) than control rats (1.0±0.1). Treatment with 3α-ethynyl-3β-hydroxyandrostan-17-one oxime restores motor coordination in hyperammonemic rats (FIG. 9A). The effects were statistically significant for the doses of 3 mg/kg (0.8±0.1 slips, p<0.05) and 20 mg/kg (0.78±0.07 slips, p<0.05).

PCS rats also show motor in-coordination in the beam walking test, with higher (p<0.01) number of slips (1.2±0.1) than sham-operated control rats (0.71±0.07). Treatment with 3α-ethynyl-3β-hydroxyandrostan-17-one oxime also restores motor coordination in PCS rats (FIG. 9B). The number of slips for the dose of 0.7 mg/kg was 0.75±0.10 (p<0.05 vs PCS rats). At 2.5 mg/Kg 3α-ethynyl-3β-hydroxyandrostan-17-one oxime also improved motor coordination, returning to values similar to sham rats (0.8±0.1 slips; p vs PCS rats=0.058) (FIG. 9B).

Example 9

Therapeutic Effect of
3α-Ethynyl-3β-Hydroxyandrostan-17-One Oxime
on the Spatial Memory and Spatial Learning of
Rats with HE and Porta-Caval Anastomosis Treatment and Testing Schedule The treatment and testing schedule were as set out in Example 8.

Spatial Memory and Learning in the Morris Water Maze Test.

The test was carried out as described by Monfort et al. (*European Journal of Neuroscience*, 2007, 25, 2103-2111) using a circular pool (160 cm diameter, 40 cm height) arbitrarily divided into four quadrants. After pre-training, the rats were trained to learn the fixed location of the invisible platform over 3 days. Training involved placing the rat into the pool facing the wall in one of the three quadrants lacking the platform. A different starting point was randomly used on each trial. Training consisted of three swims per day. Each animal was allowed a maximum of 120 seconds to find the platform and was left for 20 seconds on the platform. If a rat failed to locate the platform within 120 seconds it was manually guided to the platform by the experimenter. The time needed to find the hidden platform was recorded manually and used as a measure of learning of the task. Spatial memory was assessed 24 hours later by removing the platform and measuring the time spent by the rat in the quadrant where the platform was.

Results.

3α-Ethynyl-3β-hydroxyandrostan-17-one oxime was shown to restore spatial memory in the Morris water maze test in hyperammonemic and PCS rats.

Hyperammonemic rats showed reduced spatial memory in the Morris water maze. All groups of rats learned to find the platform and the latency to reach it was reduced along the three training days (FIG. 10A). Learning ability was slightly reduced in hyperammonemic rats, which needed more time than control to reach the platform.

Spatial memory was significantly reduced (p<0.05) in hyperammonemic rats. In the memory test hyperammonemic rats remained less time (30±2% of the time) in the right quadrant than control rats (39±2% of the time). Treatment with 3α-ethynyl-3β-hydroxyandrostan-17-one oxime restored spatial memory in the Morris water maze in hyperammonemic rats. The percentages of time spent in the correct quadrant were 41±4, 42±5 and 38±3, for 3, 10 and 20 mg/kg doses, respectively (FIG. 10B).

PCS rats also showed reduced spatial memory in the Morris water maze. All groups of rats learned to find the platform and the latency to reach it was reduced along the three training days (FIG. 10C). Spatial memory was significantly reduced (p<0.05) in PCS rats. In the memory test PCS rats remained less time (31±3% of the time) in the right quadrant than control rats (41±2% of the time). Treatment with 3α-ethynyl-3β-hydroxyandrostan-17-one oxime restored spatial memory in the Morris water maze in PCS rats. The percentages of time spent in the correct quadrant were 34±4 and 39±3, for 0.7 and 2.5 mg/kg doses, respectively (FIG. 10D).

Example 10

Therapeutic Effect of
3α-Ethynyl-3β-Hydroxyandrostan-17-One Oxime
on the Spatial Learning of Rats with HE and
Porta-Caval Anastomosis Treatment and Testing Schedule The treatment and testing schedule were as set out in Example 8.

Spatial Learning in the Radial Maze Test.

The apparatus was composed of a central area that gave access to eight equally-sized arms. The arms were 70 cm long and 10 cm wide and the central area was 30 cm in diameter. The distal extreme of each arm had a cup containing food rewards. Rats were allowed to explore the maze for 10 minutes on two consecutive days in the presence of distal cues to adapt to the maze. Training in the radial maze was composed of three trials per day on six consecutive days. The task involved locating four pellets, each placed at the end of a different arm according to a random configuration as described by Hernandez-Rabaza et al. (*Addiction Biology*, 2010, 15, 413-423). The number of working memory errors (visits to arms already visited in the same trial) were recorded and expressed as working errors.

Results

3α-Ethynyl-3β-hydroxyandrostan-17-one oxime was found to restore spatial learning in the radial maze test.

Hyperammonemic rats show reduced spatial learning in the radial maze. As shown in FIG. 11A, the number of working errors was higher in hyperammonemic than in control rats at days 1-3. All groups of rats learned along the training days and the difference between control and hyperammonemic rats was not significant after day 3. (FIG. 11A). The number of working errors in days 1-2 was higher ($p<0.05$) in hyperammonemic (18±3 errors) than in control rats (11±1.5 errors). Hyperammonemic rats treated with 3α-ethynyl-3β-hydroxyandrostan-17-one oxime behaved as controls. The number of errors (not significantly different from controls) was 6.5±2.8, 8.8±1.9 and 12±2, for 3, 10 and 20 mg/kg doses, respectively (FIG. 11B-C).

PCS rats also show reduced spatial learning in the radial maze. As shown in FIG. 11C, the number of working errors was higher in PCS rats than in sham rats at days 1 and 2. All groups of rats learned along the training days and the difference between sham and PCS rats was not significant after day 3. (FIG. 11C). The number of working errors in days 1-2 (FIG. 11D) was higher ($p<0.01$) in PCS rats (22±2 errors) than in sham rats (10±2 errors). Treatment of PCS rats with 0.7 mg/Kg of 3α-ethynyl-3β-hydroxyandrostan-17-one oxime was not enough to improve performance in the radial maze (23±2 errors). Treatment with 2.5 mg/Kg completely normalized performance of PCS rats in the radial maze (11±1 errors, $p<0.05$ vs PCS).

Example 11

Therapeutic Effect of
3α-Ethynyl-3β-Hydroxyandrostan-17-One Oxime
on the Circadian Rhythms and Nocturnal Motor
Activity in PCS Rats Treatment and Testing Schedule The treatment and testing schedule were as set out in Example 8.

Circadian Rhythms of Spontaneous Locomotor Activity.

Motor activity was measured using an actimeter (Med Associates, St. Albans, Vt.). Rats were placed individually in an open-field activity chamber (43×43×31 cm), and motor activity was recorded continuously for 14 days in conditions of light-dark (L:D), 12 h:12 h. Data were recorded at intervals of 5 minutes. Motor activity was detected by arrays of infrared motion detectors, placed in three directions, x, y and z. One ambulatory count is recorded by the apparatus when the rat interrupts three consecutive infrared detectors, in x or y position. A vertical count is recorded when rat interrupts infrared detectors in z position. The software allows measuring different parameter of motor activity, such as ambulatory counts or vertical counts (Ahabrach et al. *Journal of Neuroscience Research*, 2010, 88, 1605-14).

Results.

3α-Ethynyl-3β-hydroxyandrostan-17-one oxime was found to increase spontaneous motor activity during the night and to partially restore the circadian rhythm of PCS rats.

PCS rats show reduced motor activity (ambulatory counts) during the night (the active phase of the rats) showing 1849±176 counts, which is significantly ($p<0.05$) lower than in control rats (4546±584 counts). 3α-ethynyl-3β-hydroxyandrostan-17-one oxime at 0.7 mg/kg increased slightly ($p<0.05$) the activity in PCS rats to 2652±275 counts. 3α-ethynyl-3β-hydroxyandrostan-17-one oxime at 2.5 mg/kg did not affect ambulatory counts (2235±170 counts 3α-ethynyl-3β-hydroxyandrostan-17-one oxime) (FIGS. 12A and 12C).

The ratio of ambulatory activity during the night vs activity during the day is reduced in PCS rats, indicating altered circadian rhythm (FIG. 12B). For the control rats this ratio was 3.3±0.4 and was reduced ($p<0.001$) in PCS rats to 0.8±0.16. PCS rats treated with 3α-ethynyl-3β-hydroxyandrostan-17-one oxime showed a partial but significant improvement ($p<0.05$) in the night/day ratio of activity, reaching 1.7±0.2 and 1.6±0.3 for 0.7 and 2.5 mg/kg, respectively (FIG. 12B). This indicates partial restoration of circadian rhythm of activity.

3α-Ethynyl-3β-hydroxyandrostan-17-one oxime was also found to normalize vertical activity during the day and to partially restore the circadian rhythm of PCS rats.

PCS rats showed reduced vertical activity during the night (the active phase of the rats) showing 561±108 counts, which is significantly ($p<0.05$) lower than in control rats (1228±138 counts). 3α-Ethynyl-3β-hydroxyandrostan-17-one oxime at 0.7 mg/kg or 2.5 mg/kg did not affect vertical activity during the night (664±121 and 695±185 counts, respectively) (FIGS. 12A and 12C).

In contrast, PCS rats showed increased vertical activity during the day showing 682±114 counts, which is significantly ($p<0.05$) higher than in control rats (391±64 counts). 3α-ethynyl-3β-hydroxyandrostan-17-one oxime at 0.7 mg/kg or 2.5 mg/kg completely normalized vertical activity during the day, reaching 339±47 and 424±44 counts, respectively. (FIGS. 12A and 12C).

The ratio of vertical activity during the night vs activity during the day was also reduced in PCS rats, indicating altered circadian rhythm (FIG. 12B). For controls this ratio is 3.7±0.6 and is reduced ($p<0.001$) in PCS rats to 0.8±0.01. PCS rats treated with 3α-ethynyl-3β-hydroxyandrostan-17-one oxime showed a partial but significant improvement ($p<0.01$) in the night/day ratio of activity, reaching 2.1±0.4 and 1.9±0.6 for 0.7 and 2.5 mg/kg, respectively (FIG. 12B). This indicates partial restoration of circadian rhythm of vertical activity.

Example 12

Effect of 3α-Ethynyl-3β-Hydroxyandrostan-17-One
Oxime Treatment on Blood Ammonia
Concentration in Hyperammonemic and PCS Rats Treatment and Testing Schedule The treatment and testing schedule were as set out in Example 8.

Determination of Ammonia.

Blood ammonia was measured using the kit II Ammonia Arkray test (PocketChem BA, Arkray) using 20 µL of fresh blood following manufacturer's specifications.

Results

3α-Ethynyl-3β-hydroxyandrostan-17-one oxime was found not to affect ammonia levels in hyperammonemic and PCS rats.

Blood ammonia levels were increased ($p<0.001$) in hyperammonemic rats 167±16 µM compared to controls (47±3 µM). Treatment with 20 mg/Kg of 3α-ethynyl-3β-hydroxyandrostan-17-one oxime did not affect ammonia levels in hyperammonemic rats (139±14 µM).

Similar results were obtained in PCS rats. Blood ammonia levels were increased (p<0.001) in PCS rats (348±27 µM) compared with sham rats (125±31 µM). Treatment with 3α-ethynyl-3β-hydroxyandrostan-17-one oxime did not affect blood ammonia, which remained at 302±30 and 294±37 µM in PCS rats treated with 0.7 and 2.5 mg/Kg of 3α-ethynyl-3β-hydroxyandrostan-17-one oxime, respectively.

Example 13

3α-Ethynyl-3β-Hydroxyandrostan-17-One Oxime Concentration in Plasma and Brain Tissue in Hyperammonemic and PCS Rats after the Treatment Period Treatment and Testing Schedule The treatment and testing schedule were as set out in Example 8.

Analysis of 3α-Ethynyl-3β-Hydroxyandrostan-17-One Oxime Exposure.

At the end of the treatment period plasma was collected from the tail vein, and after sacrifice by decapitation brains were collected and immediately frozen on dry ice. For analysis of 3α-ethynyl-3β-hydroxyandrostan-17-one oxime exposure, brain tissue was homogenized with a 1:4 ratio of tissue:PBS (pH 7.4) and then extracted with a 2-fold volume of methanol:acetonitrile (1:1), while plasma was protein-precipitated with a 3-fold volume with acetonitrile. Analyses were performed by Waters ACQUITY UPLC+Waters XEVO-TQS triple quadrupole mass spectrometer (Admescope Oy, Oulu, Finland). For calculations of the amount of free 3α-ethynyl-3β-hydroxyandrostan-17-one oxime exposure in the brain the fraction unbound ($F_{ub}$) in brain homogenates were determined by dialysis, $F_{ub}$ in HA=0.70 and $F_{ub}$ in PCS=1.43% (Admescope Oy, Oulu, Finland).

Results

In hyperammonemic rats the once-daily administration of 3α-ethynyl-3β-hydroxyandrostan-17-one oxime at 3, 10 and 20 mg/Kg resulted in a dose-dependent exposure in both plasma and in brain tissue. At the time for the behavioral testing the total concentrations of 3α-ethynyl-3β-hydroxyandrostan-17-one oxime in plasma were 0.34±0.03, 1.08±0.11, 1.95±0.61 µM, respectively, and in the brain tissue the unbound concentrations of 3α-ethynyl-3β-hydroxyandrostan-17-one oxime were 6.1±1.4, 11.6±1.4, 23±5 nmol/kg, respectively, (FIG. 14A).

Also in PCS rats the exposures were dose-dependent and with the lower doses used in these rats, 0.7 and 2.5 mg/Kg, the exposures were very similar to those in the hyperammonemic rats. Total concentrations in plasma were 0.48±0.09, and 1.64±0.30 µM, at 0.7 and 2.5 mg/kg/day respectively, and unbound concentrations in the brain were 6.18±0.97, and 17±2 nmol/kg, respectively, at the time for the behavioral testing.

The invention claimed is:

1. A method of treating hepatic encephalopathy, comprising administering a pharmaceutically effective amount of 3α-ethynyl-3β-hydroxyandrostan-17-one oxime

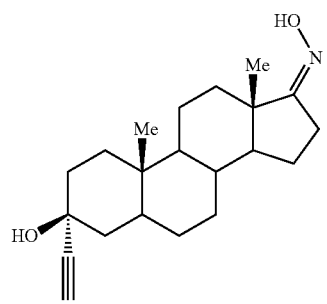 [SMILES: C#C[C@]1(O)CC[C@@]2(C)C(CCC3C2CC[C@]2(C)/C(=N\O)CCC32)C1]

or a pharmaceutically acceptable salt thereof, to a patient in need thereof.

2. The method of claim 1, wherein said hepatic encephalopathy is minimal hepatic encephalopathy.

3. The method of claim 1, wherein said hepatic encephalopathy is overt hepatic encephalopathy.

4. The method of claim 1, wherein said hepatic encephalopathy is type A hepatic encephalopathy.

5. The method of claim 1, wherein said hepatic encephalopathy is type B hepatic encephalopathy.

6. The method of claim 1, wherein said hepatic encephalopathy is type C hepatic encephalopathy.

7. The method of claim 4, wherein said patient suffers from acute liver failure.

8. The method of claim 1, wherein said patient suffers from chronic liver disease with or without acute-on-chronic liver failure.

9. The method of claim 1, wherein said compound is administered before, during or after a liver transplantation.

10. The method according to claim 1, wherein the treatment comprises the co-administration of 3α-ethynyl-3β-hydroxyandrostan-17-one oxime with an ammonia-lowering compound.

11. The method according to claim 10, wherein the ammonia-lowering compound is selected from the group consisting of rifaximin, lactulose, ornithine phenylacetate and glycerol phenyl butyrate.

12. The method according to claim 10, wherein the ammonia-lowering compound is lactulose.

13. The method according to claim 10, wherein the ammonia-lowering compound is rifaximin.

14. A method of preventing hepatic encephalopathy, comprising administering a pharmaceutically effective amount of 3α-ethynyl-3β-hydroxyandrostan-17-one oxime

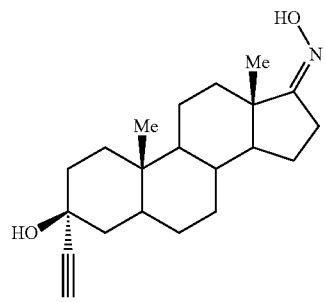 [SMILES: C#C[C@]1(O)CC[C@@]2(C)C(CCC3C2CC[C@]2(C)/C(=N\O)CCC32)C1]

or a pharmaceutically acceptable salt thereof, to a patient in need thereof.

15. The method of claim 14, wherein said hepatic encephalopathy is minimal hepatic encephalopathy.

16. The method of claim 14, wherein said hepatic encephalopathy is overt hepatic encephalopathy.

17. The method of claim 14, wherein said hepatic encephalopathy is type A hepatic encephalopathy.

18. The method of claim 14, wherein said hepatic encephalopathy is type B hepatic encephalopathy.

19. The method of claim 14, wherein said hepatic encephalopathy is type C hepatic encephalopathy.

20. The method of claim 17, wherein said patient suffers from acute liver failure.

21. The method of claim 14, wherein said patient suffers from chronic liver disease with or without acute-on-chronic liver failure.

22. The method of claim 14, wherein said compound is administered before, during or after a liver transplantation.

23. The method according to claim 14, wherein the treatment comprises the co-administration of 3α-ethynyl-3β-hydroxyandrostan-17-one oxime with an ammonia-lowering compound.

24. The method according to claim 23, wherein the ammonia-lowering compound is selected from the group consisting of rifaximin, lactulose, ornithine phenylacetate and glycerol phenyl butyrate.

25. The method according to claim 23, wherein the ammonia-lowering compound is lactulose.

26. The method according to claim 23, wherein the ammonia-lowering compound is rifaximin.

27. The method of claim 1 comprising administering to the patient a pharmaceutical composition comprising the 3α-ethynyl-3β-hydroxyandrostan-17-one oxime or a pharmaceutically acceptable salt thereof together with pharmaceutically acceptable carriers, excipients and/or diluents.

* * * * *